United States Patent [19]  
Fiato et al.

[11] Patent Number: 4,544,672  
[45] Date of Patent: Oct. 1, 1985

[54] COBALT-PROMOTED CATALYSTS FOR USE IN FISCHER-TROPSCH SLURRY PROCESS

[75] Inventors: Rocco A. Fiato, Scotch Plains; Stuart L. Soled, Madison, both of N.J.

[73] Assignee: Exxon Research and Engineering Co., Florham Park, N.J.

[21] Appl. No.: 561,191

[22] Filed: Dec. 14, 1983

[51] Int. Cl.$^4$ ................................. C07L 1/04
[52] U.S. Cl. ..................... 518/700; 502/524
[58] Field of Search ............ 518/700, 717, 720, 721

[56] References Cited

U.S. PATENT DOCUMENTS

| | | | |
|---|---|---|---|
| 2,644,829 | 7/1953 | Hogan | 518/720 |
| 2,662,090 | 12/1953 | Scharmann et al. | 260/449.6 |
| 2,686,195 | 8/1954 | McAdams | 260/449.6 |
| 2,735,862 | 2/1956 | Buchmann et al. | 260/449.6 |
| 2,850,515 | 9/1958 | Riblett | 260/449.6 |
| 4,154,751 | 5/1979 | McVicker et al. | 260/449.6 R |

FOREIGN PATENT DOCUMENTS 2050859A 1/1981 United Kingdom .

OTHER PUBLICATIONS

"The Synthesis of Light Hydrocarbons from CO and $H_2$ Mixtures over Selected Metal Catalysts", by M. K. Zaman Khan et al., ACS 173rd Symposium, Fuel Division, New Orleans, Mar. 1977.
"Mossbauer Spectroscopy of Supported Fe–Co Alloy Catalysts for Fischer-Tropsch Synthesis"—Journal of Catalysts, vol. 72, pp. 37–50, (1981)—Stanfield et al.
"Mossbauer and Magnetic Studies of Bifunctional Medium-Pore Zeolite-Iron Catalysts Used in Synthesis Gas Conversion"—Advances in Chemistry Series, 1981, pp. 573–588 by Lo et al.
"Mossbauer Effect in Iron and Dilute Iron Based Alloys"—Physics Reports Section C of Physics Letters), 12 No. 5, (1974), pp. 335–374.
Hydrocarbon Processing, May 1983, pp. 88–96.
Chem-Ing.-Tech. 49, (1977), (Nos. 6: pp. 463–468, (1977), by D. Kitzelmann et al., (German).
C. R. Acad. Sc. Paris, p. 268, (May 28, 1969), by P. Courty and B. Delmon.
"Fischer-Tropsch Synthesis with Iron-Cobalt Alloy Catalysts"—Stud. Surf. Sci Catal. 7, Part A, pp. 432–446, (1981), (English).
AIChE, 1981 Summer National Meeting, Detroit, Preprint No. 408, (English).
Journal of Materials Science 7, (1972), pp. 1383–1390, by A. C. C. Tseung, and J. R. Goldstein.
ACS Meeting, Division of Petroleum Chemistry, Mar. 1978, entitled "Catalytic Synthesis of Light Olefinic Hydrocarbons from CO and Hydrogen Over Some Iron Catalysts", by C. H. Yang and A. G. Oblad.
Journal of Catalysis 32, pp. 452–465, (1974), by J. R. Goldstein et al.
J. Phys. Chem. Solids 1959, vol. 9, pp. 165–175, by G. H. Jonker.
"The Fischer-Tropsch and Related Synthesis", by Storch, Golombic and Anderson, (Wiley), pp. 242–243.
Catal. Rev.-Syn. Eng. 21, (2), pp. 225–274, (1980).
J. Phys. Chem. Solids 1976, vol. 37, pp. 619–624, by P. J. Murray and J. W. Linnett.
"Numerical Data and Functional Relationships in Science and Technology", Landolt-Bornstein, New Series, vol. 12, part B, Magnetic and Other Properties of Oxides and Related Compounds: Spinels, Iron Oxides and Iron-Metal-Oxygen Compounds, editor K. H. Hellwege, pp. 245–250.
Kirk-Othmer, "Encyclopedia Of Chemical Technology", 3rd Edition, vol. 13, pp. 90–95.
Journal of Catalysis, vol. 72, pp. 95–110, (1981), by J. A. Amelse, L. A. Schwartz and J. B. Butt.
Hydrocarbon Processing, Nov. 1980, pp. 139–142, "Make Olefins from Syn Gas", by V. U. S. Rao and R. J. Gormley.
Z. Physik Chemie Neue Folge 112, 215–233, (1978), by Kitzelman et al., "In Situ Study of the Primary Reactions in the Hydrogenation of CO on Iron Catalysts".
J. C. S. Chem. Comm., pp. 428–430, (1983).

Primary Examiner—Howard T. Mars  
Attorney, Agent, or Firm—Robert J. North; Edward M. Corcoran

[57] ABSTRACT

Slurried low initial surface area Fe—Co spinels, containing low levels of cobalt, which are fully reduced/carburized ex situ, provide exceptionally high activity and selectivity in the conversion of $CO/H_2$ to alpha olefins in a slurry type process. These slurried unsupported iron-cobalt catalysts maintain good activity and selectivity under low pressure reaction conditions.

23 Claims, No Drawings

COBALT-PROMOTED CATALYSTS FOR USE IN FISCHER-TROPSCH SLURRY PROCESS

FIELD OF THE INVENTION

This invention relates to a Fischer-Tropsch slurry process for producing low molecular weight olefins, particularly those in the $C_2-C_4$ range, using an unsupported Group IA or IIA metal salt promoted catalyst being preferably an ex situ reduced and carbided iron-cobalt spinel, in which the atomic ratio of Fe:Co is 7:1 or above, and said spinel having initially a measured BET surface area of up to about 5 $m^2/g$ prior to said carbiding and reducing.

DISCLOSURES IN THE ART

Fischer-Tropsch processes have long been known to produce gaseous and liquid hydrocarbons containing $C_2-C_4$ olefins. Because of the importance of $C_2-C_4$ olefins, particularly as feedstocks for the chemical industry, modifications of the Fischer-Tropsch process are constantly being pursued toward the goals of maximizing $C_2-C_4$ olefins selectivity with the particular objective of maintaining high catalyst activity and stability under the reaction conditions. The main thrust of the efforts in this area has been in the area of catalyst formulation.

Coprecipitated iron-based catalysts, including those containing cobalt, are known for producing $C_2-C_4$ olefins. High levels of cobalt in an iron-cobalt alloy are known to produce enhanced selectivity to olefinic products, as described in *Stud. Surf. Sci. Catal.* 7, Pt/A, pp. 432 (1981).

Other disclosures in the art directed to coprecipitated iron-cobalt catalysts and/or alloys include: U.S. Pat. No. 2,850,515; U.S. Pat. No. 2,686,195; U.S. Pat. No. 2,662,090 and U.S. Pat. No. 2,735,862; AICHE 1981 Summer Nat'l Meeting Preprint No. 408, "The Synthesis of Light Hydrocarbons from CO and $H_2$ Mixtures over Selected Metal Catalysts" ACS 173rd Symposium, Fuel Division, New Orleans, March 1977; J. Catalysis 1981, No. 72(1), pp. 37-50; Adv. Chem. Ser. 1981, 194, 572-88; Physics Reports (Section C of Physics Letters) 12 No. 5 (1974) pp. 335-374; UK Patent Application No. 2050859A; J. Catalysis 72, 95-110 (1981); Gmelins Handbuch der Anorganische Chemie 8, Auflage (1959), pp. 59. Hydrocarbon Processing, May 1983, pp. 88-96; and Chem.-Ing.-Tech. 49 (1977) Nr. 6, pp. 463-468.

There is further disclosed a method for producing high surface metal oxides in the French article, "C. R. Acad. Sc. Paris", p. 268 (May 28, 1969) by P. Courte and B. Delmon. The article describes a process for producing high surface area metal oxides by evaporating to dryness aqueous solutions of the corresponding glycolic acid, lactic acid, malic or tartaric acid metal salts. One oxide that was prepared by their described method was $CoFe_2O_4$.

However, the above references do not describe or suggest the use of unsupported iron-cobalt single phase spinels, having an Fe:Co atomic ratio of 7:1 or above in conducting or carrying out slurry-type Fischer-Tropsch processes.

What is particularly desired in slurry type Fischer-Tropsch processes are highly active and selective Fe-Co catalysts which can be easily prepared preferably by ex situ reduction and carburization of low surface area spinel starting materials. The obtained catalysts are useful in selectively producing high levels of $C_2-C_4$ olefins and low levels of methane under the desirable combined conditions of high catalyst activity and stability.

SUMMARY OF THE INVENTION

It has been found that reduced and carbided, preferably ex situ, unsupported iron-cobalt single phase spinels containing low levels of cobalt, i.e. iron:cobalt atomic ratios of 7:1-35:1, and being promoted with Group IA or IIA metal salts, provide desirable catalyst properties in slurry type Fischer Tropsch processes. The initial spinels prior to reduction and carbiding exhibit a powder X-ray diffraction pattern isostructural with $Fe_3O_4$ and possess BET surface areas of up to 5 $m^2/g$ (square meters per gram).

The spinels are conveniently prepared in a high temperature solid state sintering reaction in a temperature range of about 100° to 600° C. between the component metal oxides and/or metals, in an inert or vacuum atmosphere. The spinels prepared in this manner can then be treated with promoter agents, such as alkali metal salts, and particularly potassium carbonate. The resulting spinels have surface areas in the range of about 0.1 to 5 $m^2/g$. The resulting combined iron and cobalt/potassium atomic ratio is desirably in the range of about 20:1 to 200:1. The promoted catalyst is then preferably reduced ex situ in a hydrogen containing gas and preferably carbided ex situ in a suitable carbiding atmosphere before use in the Fischer-Tropsch slurry process.

In accordance with this invention there is provided a process for synthesizing a hydrocarbon mixture containing $C_2-C_4$ olefins comprising the step of contacting a liquid slurry catalyst system comprised of a slurry liquid and a reduced and carbided unsupported iron-cobalt single phase spinel catalyst, or mixture thereof, containing a Group IA or IIA metal salt promotor agent, and said spinel having the initial empirical formula:

$$Fe_xCo_yO_4$$

wherein x and y are integer or decimal values, other than zero, with the provisos that the sum of x+y is 3 and the ratio of x/y is 7:1 or above, said spinel initially exhibiting an X-ray diffraction pattern substantially isostructural with that of $Fe_3O_4$ and said spinel having a measured BET surface area of up to about 5 $m^2/g$, said process being conducted with a mixture of CO and hydrogen under conditions of pressure, space velocity, and elevated temperature, for a time sufficient to produce said product $C_2-C_4$ olefins.

DESCRIPTION OF THE INVENTION AND PREFERRED EMBODIMENTS

The iron-cobalt spinels useful in the subject process are new compositions of matter which are isostructural with $Fe_3O_4$, as determined by x-ray diffractometry using copper K (alpha) radiation and exhibit a single spinel phase. They are adequately and fully described including methods of preparation in copending application Ser. No. 561,292, filed Dec. 14, 1983 and hereby incorporated by reference for that purpose. By the term "spinel" as used herein is meant a crystal structure whose general stoichiometry corresponds to $AB_2O_4$, where A and B can be the same or different cations. Included within this definition is the commonly found spinel, $MgAl_2O_4$. A and B can have the following cationic charge combinations: $A=+2$, $B=+3$, $A=+4$, $B=+2$, or $A=+6$, $B=+1$. Spinels are arranged of an approximately cubic close-packed arrangement of oxygen atoms with $\frac{1}{8}$ of the available tetrahedral interstices and $\frac{1}{2}$ of the octahedral interstices filled, and can exhibit hundreds of different phases. Further description of the spinel structure can be found in "Structural Inorganic Chemistry" by A. F. Wells, Third Edition, Oxford Press, and the Article "Crystal Chemistry and Some Magnetic Properties of Mixed Metal Oxides with the Spinel Structure" by G. Blasse, Phillips Research Review Supplement, Volume 3, pp. 1–30, (1964). By the term "isostrucural" is meant crystallizing in the same general structure type so that the arrangement of the atoms remains very similar with only minor changes in unit cell constants, bond distances and angles. By the term "single phase spinel", as used herein, is meant one structural and compositional formula, corresponding to a single spinel material into which all of the metal components are incorporated, and exhibiting one characteristic X-ray diffraction pattern.

The iron-cobalt spinels possesses a BET (nitrogen) surface area up to about 5 m$^2$/g. as determined by the well-known BET surface area measurement technique as described in the reference JACS 60, p. 309 (1938) by S. Brunauer, P. H. Emmett and E. Teller. Preferably, the spinel has a surface area of about 0.1 to 1 m$^2$/g. This range of surface area generally corresponds to a particle size range of about 1 to 10 microns.

The iron to cobalt atomic ratio of the metals in the spinel is about 7:1 or above and is preferably in the range of about 7:1 to 35:1.

The spinel can be represented by the formula: $Fe_xCo_yO_4$, wherein x and y are decimal or integer values, other than zero, and wherein the sum of x plus y is 3, and the ratio of x to y is 7:1 or above and preferably being about 7:1 to 35:1. Particularly preferred is where the iron to cobalt atomic ratio is about 19 to 20:1.

Representative examples of the various spinels corresponding to the formula are $Fe_{2.85}Co_{0.15}O_4$, $Fe_{2.625}Co_{0.375}O_4$, $Fe_{2.97}Co_{0.03}O_4$, $Fe_{2.25}Co_{0.75}O_4$.

Physical properties in general of these subject spinels are similar to those of $Fe_3O_4$ and include a melting point above 1400° C. and a color of black to brownish-red.

The iron-cobalt spinels are used in unsupported form in $H_2/CO$ hydrocarbon synthesis.

A promotor agent can also be used in the composition and can be used to particularly promote olefin formation, in the process. Representative examples of classes of suitable promoter agents include carbonates, bicarbonates, organic acid salts and inorganic acid salts, e.g. acetates, nitrates, halides, sulfates, and hydroxide salts of Group IA and IIA metals including lithium, sodium, potassium, rubidium, cesium, barium, strontium, magnesium and the like.

Representative examples of specific promotor agents are potassium carbonate, potassium sulfate, potassium bicarbonate, cesium chloride, rubidium nitrate, lithium acetate, potassium hydroxide and the like. A particularly preferred promoter agent is potassium carbonate. The promoter, if used, is generally present in about a 0.1 to 10 gram-atom % of the total metal gram-atoms present. A preferred level of promoter agent is in the range of 1 to 2 gram-atom % of the total metals gram-atoms content. In the empirical formulas used herein, the amount of promoter agent, e.g., potassium, is expressed in terms of gram-atom percent based on the total gram-atoms of metals used. Thus, 1 gram-atom percent of potassium signifies the presence of 1 gram-atom of potassium per 100 total gram-atoms of combined gram-atoms of Fe and Co. Therefore, the symbol "/1%K" as used herein indicates 1 gram-atom percent potassium based on each 100 gram-atoms of the total gram-atoms of iron and cobalt present.

A particularly preferred spinel composition useful in the subject process is $Fe_{2.85}Co_{0.15}O_4/1$ gram-atom % potassium.

The utility of these spinels is their ability upon preferably ex situ reduction and carbiding, which can be done independently or concurrently, to form active catalysts in a slurry type Fischer-Tropsch process for making $C_2$–$C_4$ olefins from CO/hydrogen, in which lengthy in situ pretreatment, reduction and carbiding steps can be eliminated. By the term "ex situ" as used herein is meant outside of the slurry medium used in the slurry Fischer-Tropsch process.

The spinel catalyst precursor is prepared by a solid state high temperature reaction between the component oxides, e.g. $Fe_3O_4$ and $Co_3O_4$, or a mixture of iron metal, cobalt oxide and iron oxide, i.e. Fe, $Co_3O_4$ and $Fe_2O_3$, or a mixture of cobalt metal, iron oxides and cobalt oxide, i.e. CoO, $Fe_3O_4$, $Fe_2O_3$ and $Co_3O_4$ in the correct stoichiometric metals and oxygen ratios to result in the empirical formula for the composition formula as given above. This procedure is adequately detailed and described in copending application Ser. No. 561,292, hereby incorporated by references for that purpose. The reaction is conducted at temperatures in the range of about 600° to 1100° C. and preferably from about 800° to 900° C., in an inert gas or vacuum environment. Example of useful inert gases are helium, nitrogen, argon and the like. The solid state high temperature reaction "sintering" should be performed on thoroughly mixed samples of the metal oxides and/or metal and metal oxide mixtures. A preferred method of forming the mixture is by intimate grinding. The sintering reaction should be conducted until a powder X-ray diffraction pattern indicates a single spinel phase is formed which generally requires about an 8 to 24 hour period and preferably about 12 to 18 hour period. Generally, at the end of each reaction period the material is thoroughly ground and reheated an additional 1 to 5 cycles or until x-ray diffraction reveals the presence of a single spinel phase.

The ex situ reduction step of the iron-cobalt spinel can be conducted in a reducing atmosphere at elevated temperature, generally in a temperature range of about 200° to 500° C. and preferably 350° to 450° C. The reduction step can be carried out with various reducing gases including hydrogen, hydrogen/CO, and CO and mixtures thereof. Preferably, hydrogen gas, either by itself or in an inert carrier medium such as helium, neon, argon, or nitrogen, is preferably used. The pressure of the reducing gas in this procedure may be in the range of 1.5 to 1000 psig and preferably in the range of 15 to 150 psig. The reducing gas feed rate may be in the range of 1–10,000 V/V/hr and preferably in the range of 10–1000 V/V/hr.

The subsequent carbiding step of the iron-cobalt catalyst can be conducted by carbiding the reduced iron-cobalt spinel, described hereinabove, by heating at elevated temperature in a suitable carbiding atmosphere.

Carbiding atmospheres which can be used include CO/hydrogen, aliphatic hydrocarbons, acetylene, aromatic hydrocarbons, and the like. A preferred carbiding atmosphere is Co/hydrogen. When using a Co/hydrogen carbiding atmosphere, mixtures of CO/hydrogen can be used in a 10:1 to 10:10 molar volume ratio. A preferred ratio used for carbiding purposes is 1:1 molar ratio.

The carbiding step is generally conducted at a temperature of 300° to 450° C. and preferably 350° to 400° C. The pressure is generally about 0.30 psig, and a space velocity of about 200–1000 V/V/hr are chosen in order to completely carbide the reduced iron-cobalt spinel which can be subjected to X-ray diffractometry to determine when the material becomes isomorphous with chi-$Fe_5C_2$. At carbiding temperatures above about 450° C., the resulting Hagg type carbide, $Fe_{5-(5/3)y}Co_{(5/3)y}C_2$, becomes unstable and can rearrange crystallographically to the corresponding cementite type structure, $Fe_{3-y}Co_yC$. Also, in the ex situ carbiding step, a significant amount of carbon is also formed on the surface of the catalyst which tends to increase the surface area of the reduced, carbided catalyst.

The above-described reduced spinel and carbided spinel, when prepared ex situ are generally pyrophoric and inconvenient to handle. In that case, the material is generally passivated by contact with 1 volume oxygen in 100 volumes of helium for a sufficient time to reduce or eliminate the pyrophoric nature. Generally, the oxygen used in the passivating process is used in an inert gas stream carrier such as helium for a sufficient time to cause passivation. Generally, this is conducted at room temperature and atmospheric pressure and space velocity which are convenient and easy to control and to result in an efficient process needed for complete passivation.

The details of the slurry process described herein are similar to those described in copending patent application, Ser. No. 561,192 filed Dec. 14, 1983, in a Fischer-Tropsch slurry process, hereby incorporated by reference for that purpose.

The subject process of the instant invention is a Fischer-Tropsch slurry process for producing $C_2$–$C_4$ olefins by utilizing the reduced and carbided, iron-cobalt spinel catalyst described hereinabove, wherein the catalyst is suspended in a liquid hydrocarbon and the CO/hydrogen mixture forced through the catalyst slurry allowing good contact between the CO/hydrogen and the catalyst to initate and maintain the hydrocarbon synthesis process.

Advantages of a slurry process over that of a fixed bed process are that there is better control of the exothermic heat produced in the Fischer-Tropsch process during the reaction and better control over catalyst activity maintenance by allowing continuous recycle, recovery and rejuvenation procedures to be implemented. The slurry process can be operated in a batch or in a continuous cycle, and in the continuous cycle, the entire slurry can be circulated in the system allowing for better control of the primary products residence time in the reaction zone.

The slurry liquid used in the process is a liquid at the reaction temperature, must be chemically inert under the reaction conditions and must be a relatively good solvent for CO/hydrogen and possess good slurrying and dispersing properties for the finely divided catalyst. Representative classes of organic liquids which can be utilized are high boiling paraffins, aromatic hydrocarbons, ethers, amines, or mixtures thereof. The high boiling paraffins include $C_{10}$–$C_{50}$ linear or branched paraffinic hydrocarbons; the aromatic hydrocarbons include $C_7$–$C_{20}$ single ring and multi- and fused ring aromatic hydrocarbons; the ethers include aromatic ethers and substituted aromatic ethers where the ether oxygen is sterically hindered from being hydrogenated; the amines include long chain amines which can be primary, secondary, and tertiary amines, wherein primary amines preferably contain at least a $C_{12}$ alkyl group in length, secondary amines preferably contain at least two alkyl groups being $C_9$ or greater in length, and tertiary amines preferably contain at least three alkyl groups being $C_6$ or higher in length. The slurry liquid can contain N and O in the molecular structure but not S, P, As or Sb, since these are poisons in the slurry process. Representative examples of specific liquid slurry solvents useful are dodecane, tetradecane, hexadecane, octadecane, cosane, tetracosane, octacosane, triacontane, dotriacontane, hexatriacontane, tetracontane, tetratetracontane, toluene, o-, m-, and p-xylene, mesitylene, $C_1$–$C_{13}$ mono- and multi-alkyl substituted benzenes, dodecylbenzene, naphthalene, anthracene, biphenyl, diphenylether, dodecylamine, dinonylamine, trioctylamine, and the like. A preferred liquid hydrocarbon slurry solvent is octacosane.

The amount of catalyst used in the liquid hydrocarbon slurry solvent is generally about 10 to 60 g. of dry catalyst per 500 g. slurry liquid. Preferably about 30 to 50 g. dry catalyst per 500 g. slurry liquid slurry is utilized, being in about a respective 5:1 to 10:1 weight ratio.

The slurry system, comprised of the slurry liquid and finally divided catalyst, is generally stirred to promote good dispersion during the pretreatment process to avoid catalyst settling and to eliminate mass transport limitations between the gas and liquid phases. In a typical laboratory unit the rate of stirring is generally carried out in the range of about 600 to 1200 rpm and preferably 1000 to 1200 rpm.

Prior to the CO/hydrogen hydrocarbon synthesis run, the preferably ex situ reduced and carbided iron-cobalt catalyst is generally conditioned in the slurry by purging with nitrogen to remove reactive oxygen-containing gases and then the temperature is increased while stirring to the reaction temperature range. Then the system is generally subjected to a hydrogen treatment for a sufficient time to insure complete removal of any surface metal oxide present which would interfere in hydrocarbon synthesis. The pressure and space velocity during the inert gas-hydrogen conditioning step are not critical and can be utilized in the range which is actually used during actual hydrocarbon synthesis.

Following the hydrogen reduction step, the Co/hydrogen feedstream is introduced into the slurry catalyst chamber and the pressure, space velocity, temperature, and hydrogen/CO molar ratio is then adjusted, as desired, for hydrocarbon synthesis conditions.

In the process, the hydrocarbon and CO are used in a molar ratio in the gaseous feedstream in about a 10:1 to 1:10 molar ratio, preferably 3:1 to 0.5:1, and particularly preferred 1:1 to 2:1 molar ratio.

The temperature in the process is generally in the range of about 200° to 300° C., preferably being 230° to 270° C., and particularly preferred of about 240°–260° C. Higher temperature ranges can also be used but tend to lead to lighter products and more methane, lower temperature ranges can also be used but tend to lead to lower activity and wax formation.

The pressure useful in the process is generally conducted in the range of about 50 to 400 psig and preferably about 70 to 225 psig. Higher pressures can also be used but tend to lead to waxy materials particularly in combination with lower temperature.

The space velocity, expressed as standard hourly space velocity (SHSV), used in the process is generally about 100 to 4,000 volumes of gaseous feedstream/per volume of dry catalyst in the slurry/per hour and is preferably in the range of about 400 to 1,200 v/v/hr, and preferably in the range of about 400 to 1,200 v/v/hr, and particularly preferred of 800–1,2000 v/v/hr. Higher lower % CO conversions, and lower space velocities can also be used but tend to lead to more paraffinic products.

Generally, after the pretreatment the CO/hydrogen feedstream is introduced to initiate and maintain hydrocarbon synthesis. By the use of the above-described catalysts in the system, the activity maintenance is very good and on a laboratory scale, e.g., 500 cc of slurry containing 50 g of catalyst described herein, 30 days of continuous run have been observed without significant decline in percent CO conversion activity while maintaining good $C_2$–$C_4$ olefin synthesis activity.

The present CO conversion obtainable in the subject process, while providing substantial quantities of $C_2$–$C_4$ olefins, ranges from about 30 to 60 percent or higher.

"Total hydrocarbons" produced in the process is related to the selectivity of percent CO conversion to hydrocarbons being hydrocarbons from $C_1$ to about $C_{40}$ inclusive and is generally about 0 to 75 percent of the total CO converted, the remainder being converted to $CO_2$.

The percent $C_2$–$C_4$ hydrocarbons of the total hydrocarbons produced including methane and above is about 10 to 30 wt. %. The percent of $C_2$–$C_4$ olefins produced, of the $C_2$–$C_4$ total hydrocarbons produced is about 80 to 90 wt. %. The olefins produced in the process are substantially alpha olefins.

The selectivity to methane based on the amount of CO conversion is about 1 to 10 weight percent of total hydrocarbons, produced. Preferably about 5 percent, and lower, methane is produced in the process.

$C_5^+$ hydrocarbon fraction in the process is generally produced in about 10 to 60 percent. The olefin content of the $C_5^+$ fraction is generally in the range of 40 to 60 wt. % of total $C_5^+$ hydrocarbons. A preferred amount is about 60%, and comprising substantially $C_5^+$ alpha-olefins.

As discussed above, the percent selectivity to $CO_2$ formation in the process is about 40 to 70 percent of CO converted.

Preferably, the reaction process variables are adjusted to minimize $CO_2$ production, minimize methane production, maximize percent CO conversion, and maximize percent $C_2$–$C_4$ olefin selectivity, while achieving activity maintenance in the catalyst system.

Generally, this format can be derived in a preferred mode of operating the process where the slurry liquid used is hexadecane, the catalyst used is ex situ reduced, carbided $Fe_{2.85}Co_{0.15}O_4$/1% $K_2CO_3$ wherein the iron-cobalt spinel has an initial BET surface area less than 5 m²/g., the catalyst/liquid weight ratio is 40/100, the system is stirred at 600 rpm, and the pretreatment procedure is conducted in situ in a single step using 9:1 $H_2$/$H_2$, at 220° C., atmospheric pressure, 1200 v/v/hr. space velocity for a period 1–2 hrs., and the olefins synthesis process conducted at a hydrogen:CO molar ratio of 1:1, a temperature of about 245° C., a pressure of about 70 psig, and space velocity 1200 v/v/hr. By carrying out the above process in the stated variable ranges efficient activity maintenance and production of $C_2$–$C_4$ olefins can be achieved.

The effluent gases in the process exiting from the reactor may be recycled if desired to the reactor for further CO hydrocarbon synthesis.

Methods for collecting the products in the process are known in the art and include fractional distallation, and the like. Methods for analyzing the product liquid hydrocarbons and gaseous streams are also known in the art and generally include gas chromatography, liquid chromatography, high pressure liquid chromatography and the like.

Apparatus useful in the preferred process is any conventional slurry-type reactor, being horizontal or vertical, being stationary or cyclical, in catalyst slurry. Other apparatus not specifically described herein will be obvious to one skilled in the art from a reading of this disclosure.

The following Examples are illustrative of the best mode of carrying out the invention as contemplated by us and should not be construed as being limitations on the scope and spirit of the instant invention.

EXAMPLE 1

1. Preparation of the Spinel

Solid solutions with the generic formula: $Fe_{3-y}Co_yO_4$ were prepared by the following procedure. Mixtures of $Fe_2O_3$, Fe metal and $Co_3O_4$ in the following molar ratios, $(4/3 - 4y/9)$ $Fe_2O_3 + 1/3$ $(1 - y/3)Fe + y/3$ $Co_3O_4$, where the value of y was: 0; 0.03; 0.150; 0.375; and 0.750; corresponding to the following respective weight proportions (in grams): $Fe_2O_3$; Fe metal; and $Co_3O_4$; 21.080, 1.8400, 0.000; 22.750, 1.9881, 0.2599; 21.797, 1.9059, 1.2974; 20.0163, 1.7502, 3.2338; 11.381, 0.9590, 4.2904. The materials (reagent quality from Alfa Chemicals) were well mixed, placed into a quartz tube, evacuated to $10^{-3}$ torr, sealed under vacuum and then heated to 800° C. for 24 hours. The resulting solids were isolated after cooling and breaking open the tube, ground to a powder, and resubjected to the same high temperature sintering at 800° to 1000° C. for 24 hours. Powder X-ray diffraction analysis was then conducted to ensure that the material was isostructural with a pure standard of $Fe_3O_4$. The catalyst powder was then impregnated with aqueous $K_2CO_3$ to achieve the desired potassium loading level (being about 1 gram-atom percent), and then dried. The measured BET surface areas (nitrogen) were in the range from about 0.25 to 0.30 m²/g. Individual spinels and their resulting surface areas are listed below in Table I.

The powder X-ray diffraction spectrum of each of the obtained Fe-Co spinels showed that they were each a single spinel phase isostructural with $Fe_3O_4$. They differed from one another in slight shifts of the two-theta reflection peaks without altering the overall profile.

TABLE I

| | $Fe_{3-y}Co_yO_4$/1% K | |
|---|---|---|
| Spinel | y | BET (m²/g.) |
| Control | 0.00 | 0.27 |
| A | 0.0275 | 0.30 |
| B | 0.150 | 0.29 |
| C | 0.375 | 0.25 |
| D | 0.750 | 0.28 |

2. Reduction of Spinel

The above obtained Spinel B was reduced at 400° C. in a stream of 15 volume percent hydrogen/85% helium for 4 hours. One percent of oxygen in helium was introduced at room temperature for one hour to passivate the material. The X-ray of the resulting material was isostructural with alpha iron.

3. Preparation of Carbide

The above reduced Spinel B was treated at 400° C. in a stream of 15 volume percent hydrogen/80% helium/5% CO at 200 v/v/hr. for four hours. Following this the sample was cooled to room temperature and 1.0% oxygen in helium was introduced for one hour to passivate the material. The X-ray diffraction pattern of the resulting material was isostructural with chi-$Fe_5C_2$. The measured BET nitrogen surface area of the material, including the carbide $Fe_{(5)-(5/3)y}Co_{(5/3)y}C_2$ and deposited carbon, was 173 $m^2/g$.

EXAMPLE 2

A slurry reactor, being a 300 cc Parr CSTR (continuous stirred tank reactor) was charged with 50 g of octacosane and 5.0 g. of the resulting reduced, carbided, Spinel B, described above. The system was purged with nitrogen and then $H_2$ while the temperature was increased from room temperature to 220° C., where the system was maintained under these conditions with stirring for a one-hr period at 600 rpm to insure reduction. The system was then placed under CO hydrogenation reaction conditions by adjusting the reaction temperature to 270° C., the $H_2$/CO volume ratio to 1:1, the space velocity to 1200 V gaseous feedstream/V dry catalyst/hr, the pressure to 70 psig, and the slurry stirrer speed to 600 rpm in the octacosane solvent. The effluent gas from the reactor was monitored by an HP-5840A Refinery Gas Analyzer to determine percent CO conversion and the nature of the hydrocarbon products. The selectivity weight percentages of product hydrocarbons exclude $CO_2$ as a product.

A second run was conducted using a reduced, carbided spinel of the same empirical formula, $Fe_{2.85}Co_{0.15}O_4/1\%$ K, and reduced and carbided by the same above-described procedure, but having an initial spinel BET surface area of above 100 $m^2/g$. Preparation and description of this compound is fully given in co-pending patent application Ser. No. 561,292, hereby incorporated by reference for this purpose.

The results are listed below in Table II.

TABLE II

Comparative Study of Fe—Co Catalysts from High and Low Surface Spinel Precursors

| | $Fe_{2.85}Co_{0.15}O_4/1\%$ K | |
|---|---|---|
| Spinel (Surface Area) | Precursor 100+ $m^2/g$ | B |
| % CO Conversion | 45 | 44 |
| % CO to $CO_2$ | 26 | 29 |
| % CO to HC | 19 | 15 |
| Wt % Selectivity | — | — |
| $CH_4$ | 4.4 | 5.9 |
| $C_2-C_4$ | 19.3 | 25 |
| $C_5+$ | 76.3 | 69.1 |
| % Olefin in $C_2-C_4$ | 90 | 90 |

Conditions:
250° C., 1200 v/g CAT/hr, 1:1 $H_2$:CO, 70 psig, 600 RPM, octacosane solvent. Catalysts subjected to ex situ $H_2$ treatment at 300+° C. followed by ex situ $H_2$/CO treatment 350+° C. to affect complete reduction-carburization.

The results in Table II indicate that catalysts prepared from low and high surface area Fe—Co spinels provide comparable performance when they are fully ex situ prereduced and carburized.

As is seen, the catalyst derived from the low surface area precursor generated more $CO_2$, less $C_5+$ hydrocarbons, but more $C_2-C_4$ olefins than the catalyst generated from the high surface area precursor, under the stated reaction conditions.

EXAMPLE 3

Utilizing the catalysts, apparatus, pretreatment and general CO hydrogenation conditions described in Example 2, the following runs were carried out utilizing the specific process conditions listed below in Table III. The conversion for Catalyst B under the stated conditions was too low for accurate determination of products (NA=not available).

TABLE III

Comparative Study of High Surface Area Oxide Catalysts

| Catalyst Surface Area | $Fe_{2.85}Co_{.15}O_4/1\%$ K 100+ $m^2/g$ | $Fe_3O_4/1\%$ K 100+ $m^2/g$ | B 0.29 $m^2/g$ |
|---|---|---|---|
| % CO Conversion | 60.0 | 8.0 | 4.0 |
| Wt. % Selectivity | | | |
| $CH_4$ | 1.8 | 4.0 | NA |
| $C_2-C_4$ | 8.0 | 15 | NA |
| $C_5+$ | 30.2 | 11 | NA |
| $CO_2$ | 60.0 | 65 | NA |
| % Olefin in $C_2-C_4$ | 8.8 | 80 | NA |

Conditions:
250° C., 1200 V/G CAT/hr, 2:1 $H_2$:CO, 70 psig, 600 RPM octacosane. Catalyst charged to reactor as oxide, treated in situ with $H_2$ at 100 psig at 200° C. for 1 hr before use.

As is seen, the catalysts derived from low surface area spinels, with added cobalt, gave low activity when employed directly under the conditions described. By contrast, catalysts derived from the high surface area Fe-Co spinels exhibited high activity when employed under the above conditions. However, the enhanced activity effect is not due to the high surface area alone, but primarily to the presence of cobalt, since the high surface area cobalt-free catalyst also exhibited low activity.

What is claimed is:

1. A slurry process for synthesizing a hydrocarbon mixture containing $C_2-C_4$ olefins comprising the step of contacting a liquid slurry catalyst system, comprised of a slurry liquid and a carbided and reduced, unsupported iron-cobalt single phase spinel catalyst containing a Group IA or IIA metal salt promoter agent, and said spinel having the initial empirical formula:

$$Fe_xCo_yO_4$$

wherein x and y are integer or decimal values, other than zero, with the provisos that the sum of x+y is 3 and the ratio of x/y is 7:1 or above, said spinel exhibiting a single phase X-ray diffraction pattern substantially isostructural with that of $Fe_3O_4$ and said spinel having a measured BET surface area of up to 5 $m^2/g$, said process being conducted with a mixture of CO and hydrogen under conditions of pressure, space velocity, and elevated temperature, for a time sufficient to produce said product $C_2-C_4$ olefins.

2. The process of claim 1 wherein said spinel catalyst is reduced and carbided ex situ of the slurry liquid prior to the process.

3. The process of claim 1 wherein said hydrogen and CO are present in a $H_2/CO$ molar ratio of about 1:10 to 10:1.

4. The process of claim 1 wherein said temperature is in a range of about 200° C. to 300° C.

5. The process of claim 1 wherein said pressure is in a range of about 50 to 400 psig.

6. The process of claim 1 wherein said standard hourly space velocity is in the range of about 100 to 4000 V/V/hr.

7. The process of claim 1 wherein said spinel is of the formula: $Fe_xCo_yO_4$ wherein x and y are integer or decimal values, other than zero, the sum of $x+y$ is 3 and the ratio of $x/y$ is 7:1–35:1.

8. The process of claim 7 wherein the ratio $x/y$ is 15–20:1.

9. The process of claim 7 wherein said spinel is of the formula: $Fe_{2.85}Co_{0.15}O_4$, $Fe_{2.625}Co_{0.375}O_4$, $Fe_{2.97}Co_{0.03}O_4$, $Fe_{2.25}Co_{0.75}O_4$.

10. The process of claim 1 wherein said promoter agent is present in about 0.1 to 10 gram-atom % of the metal ion the total gram-atom metals content.

11. The process of claim 10, wherein said promoter agent is selected from bicarbonates, carbonates, organic acid salts, inorganic acid salts, nitrates, sulfates, halides and hydroxides of Group IA and IIA metals.

12. The process of claim 11 wherein said promoter agent is potassium carbonate.

13. The process of claim 1 wherein said carbided, reduced spinel is isostructural with $Fe_5C_2$, or $Fe_3C$, as determined by X-ray diffractometry.

14. The process of claim 1 wherein said spinel has an initial BET surface area of about 0.1 to 1 $m^2/g$.

15. The process of claim 1 wherein said reduced and carbided catalyst composite has a BET surface area of about 5 to 300 $m^2/g$.

16. The process of claim 1 wherein said slurry liquid is selected from high boiling liquid paraffins, aromatic hydrocarbons, ethers, amines, or mixtures thereof.

17. The process of claim 16 wherein said high boiling liquid paraffins are $C_{12}$–$C_{60}$ linear or branched saturated aliphatic hydrocarbons.

18. The process of claim 17 wherein said hydrocarbon slurry liquid is selected from octacosane, hexadecane, or mixtures thereof.

19. The process of claim 1 wherein the weight ratio of slurry liquid: catalyst taken as the dry basis, is the range of about 10:1 to 5:1.

20. The process of claim 1 wherein said product hydrocarbon mixture contains about 30 wt % or above $C_2$–$C_{20}$ olefins.

21. The process of claim 1 wherein said product hydrocarbon mixture contains 25 wt. % $C_2$–$C_4$ hydrocarbons of the total weight of hydrocarbons produced.

22. The process of claim 21 wherein said $C_2$–$C_4$ hydrocarbons contain $C_2$–$C_4$ olefins as 80 wt. % of total $C_2$–$C_4$ hydrocarbons.

23. A process for synthesizing a hydrocarbon mixture containing $C_2$–$C_4$ olefins comprising the step of contacting a liquid slurry catalyst system, comprised of octacosane and ex situ reduced and carbided unsupported $Fe_{2.85}Co_{0.15}O_4$/1% K single phase spinel catalyst having a measured BET surface area of up to 5 $m^2/g$, with a 1:1 $H_2/CO$ mixture at 250° C., 1200 v/v/hr., 70 psig, for a sufficient time to produce said $C_2$–$C_4$ olefins.

* * * * *